(12) United States Patent
Lee et al.

(10) Patent No.: US 7,314,638 B2
(45) Date of Patent: Jan. 1, 2008

(54) PREPARING METHOD FOR CONTROLLED RELEASED TYPE TABLET TAMSULOSIN HCL AND THE TABLET THEREOF

(75) Inventors: Byoung-Suk Lee, Seoul (KR); Ah-Ram Lee, Incheon (KR); Jong-Sik Park, Seoul (KR); Eun-Ju Kim, Suwon (KR); Hyung-Joon Gil, Seoul (KR)

(73) Assignee: Kyungdong Pharm. Co., Ltd. (KR)

( * ) Notice: Subject to any disclaimer, the term of this patent is extended or adjusted under 35 U.S.C. 154(b) by 199 days.

(21) Appl. No.: 10/565,987

(22) PCT Filed: Jun. 15, 2004

(86) PCT No.: PCT/KR2004/001421

§ 371 (c)(1),
(2), (4) Date: Jan. 24, 2006

(87) PCT Pub. No.: WO2005/013960

PCT Pub. Date: Feb. 17, 2005

(65) Prior Publication Data

US 2006/0204570 A1    Sep. 14, 2006

(30) Foreign Application Priority Data

Aug. 12, 2003   (KR) .................... 10-2003-0055579
Apr. 7, 2004    (KR) .................... 10-2004-0023668

(51) Int. Cl.
| | |
|---|---|
| A61K 31/18 | (2006.01) |
| A61K 9/22 | (2006.01) |
| A61K 9/24 | (2006.01) |
| A61K 47/14 | (2006.01) |
| A61P 13/00 | (2006.01) |
| A61P 13/08 | (2006.01) |

(52) U.S. Cl. .................. 424/468; 424/472; 424/482; 514/603; 514/786; 514/960; 514/961; 514/964

(58) Field of Classification Search ............ 514/603; 424/468, 472
See application file for complete search history.

(56) References Cited

U.S. PATENT DOCUMENTS

| 4,772,475 | A | * | 9/1988 | Fukui et al. ............ 424/468 |
| 6,569,463 | B2 | * | 5/2003 | Patel et al. ............ 424/497 |
| 7,255,876 | B2 | * | 8/2007 | Shinoda et al. .......... 424/464 |
| 2003/0064097 | A1 | * | 4/2003 | Patel et al. ............ 424/465 |
| 2007/0196500 | A1 | * | 8/2007 | Woo et al. ............. 424/490 |

OTHER PUBLICATIONS

Derwent abstract 2003-565433; abstracting KR 2002063753 (2002).*
HCAPLUS abstract 2004:969522; abstracting KR 2002063753 (2002).*
Medline abstract 2007132208 (2007).*

* cited by examiner

*Primary Examiner*—John Pak
(74) *Attorney, Agent, or Firm*—Galgano & Associates, PLLC

(57) ABSTRACT

The present invention relates to a simple and effective method for preparing a tamsulosin HCl sustained-release tablet and a tamsulosin HCl sustained-release tablet produced thereby. The method comprises the steps of: dissolving tamsulosin HCl as an active ingredient in an organic solvent; dissolving the tamsulosin HCl solution in hydroxypropylmethylcellulose phthalate to prepare a binder solution; and kneading the binder solution with a hydroxypropylmethylcellulose phthalate/glyceryl dibehenate mixture as an excipient and allows tamsulosin HCl to be released at uniformly controlled amounts in a subtained-release manner in vivo by controlling drug release rate according to different pH environments in vivo, so that it shows improved bioavailability and minimized side effects.

18 Claims, 2 Drawing Sheets

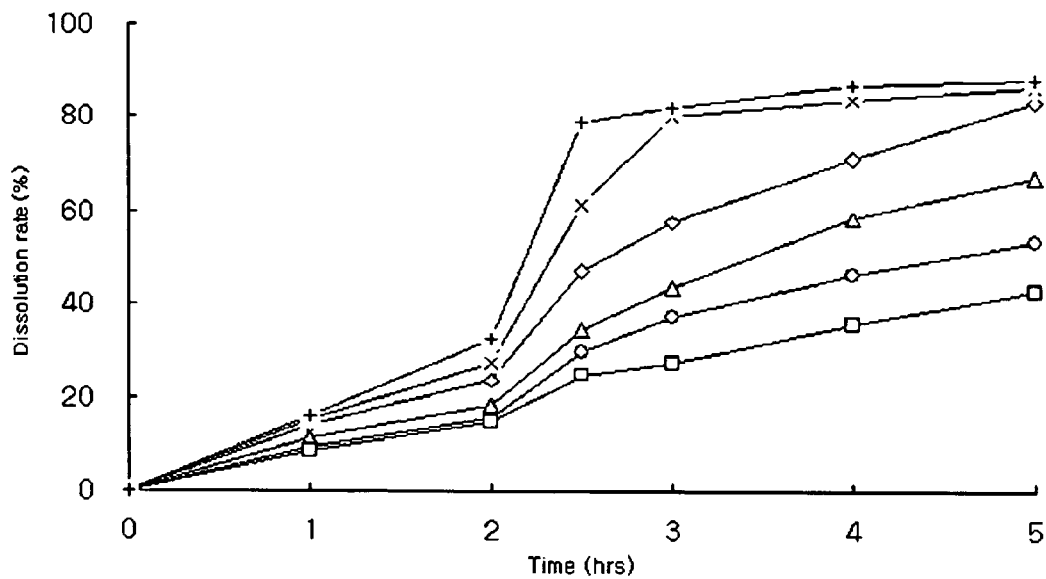
[Fig. 1]
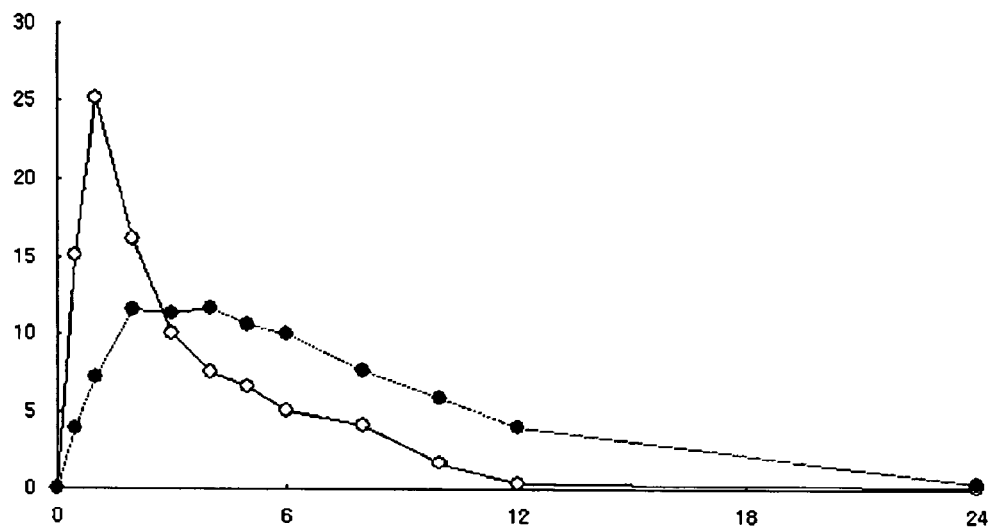
[Fig. 2]

[Fig. 3]
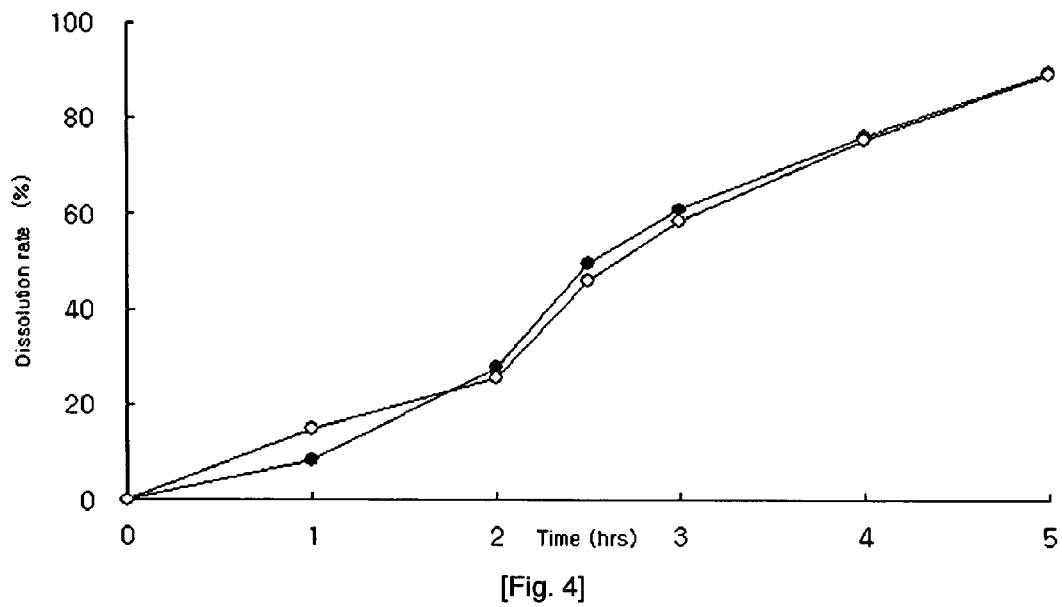
[Fig. 4]
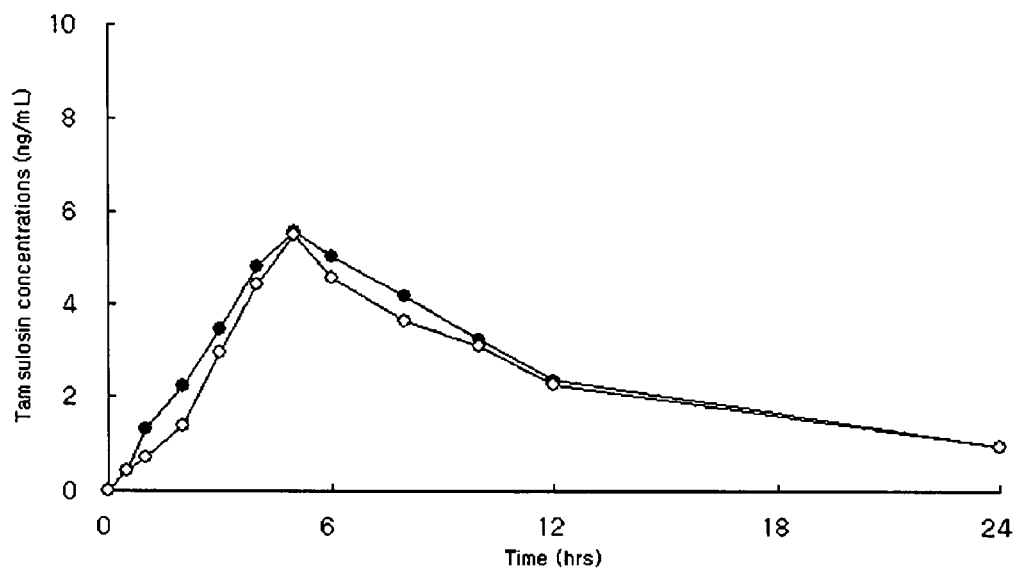

PREPARING METHOD FOR CONTROLLED RELEASED TYPE TABLET TAMSULOSIN HCL AND THE TABLET THEREOF

This application is a 371 of PCT/KR04/01421, filed on Jun. 15, 2004.

TECHNICAL FIELD

The present invention relates to a method for preparing a tamsulosin hydrochloride (HCl) sustained-release tablet and a tamsulosin HCl sustained-release tablet prepared thereby. More particularly, the present invention relates to a method for preparing a tamsulosin HCl sustained-release tablet, which comprises the steps of: dissolving tamsulosin HCl as an active ingredient in an organic solvent; dissolving the tamsulosin HCl solution in hydroxypropylmethylcellulose phthalate to prepare a binder solution; and kneading the binder solution with a hydroxypropylmethylcellulose phthalate/glyceryl dibehenate mixture as an expedient. The tamsulosin HCl sustained-release tablet prepared according to the present invention allows a low dose of the tamsulosin HCl as an active drug to be released at uniformly controlled amounts in a sustained-release manner in vivo by controlling drug release rate according to different pH environments in vivo, so that it shows improved bioavailability and minimized side effects.

BACKGROUND ART

Tamsulosin HCl ((−)-(R)-5-[2-((2-(o-ethoxyphenoxy)ethyl)amino)propyl]-2-methoxy-benzenesulfonamide hydrochloride), the left-handed optical isomers of the following formula (I), is an active drug of improving or mitigating urinary dysfunction caused by anatomical or mechanical urinary obstruction by bladder neck obstruction, and functional urinary obstruction by the excessive contraction of bladder neck, prostatic stroma and proliferated smooth muscle distributed in the urethra. Its action mechanism is under the control of autonomic sympathetic nerve, and it selectively blocks an alpha 1-a drenergic receptor to inhibit the contraction of bladder neck, prostatic smooth muscle and urinary smooth muscle, thus relaxing the bladder neck, the prostate and the urethra, thereby improving or mitigating urinary dysfunction symptoms. It is currently sold in the form of a capsule formulation that is administered one time a day.

[Formula I]

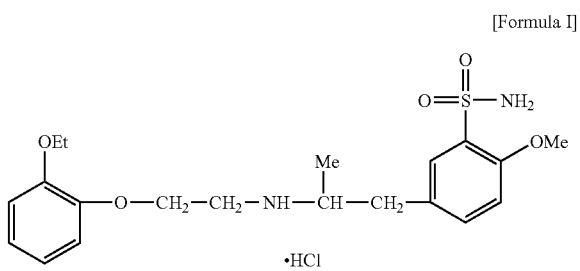

Generally, in order that an administered drug exhibits the greatest effect, the in vivo concentration of the drug needs to be maintained constantly over an extended period of time. For this, control of the release rate of the drug from a formulation containing the drug is necessary, and thus, extensive studies to develop a variety of sustained-release formulations have been conducted in the art.

Of such sustained-release formulations, an oral sustained-release formulation whose drug release is mainly controlled throughout the gastrointestinal tract can increase the patient's compliance with drug treatment, reduce the number of treatments to be administered, and avoid the excessively high concentration of a drug in blood. Accordingly, the oral formulation can not only reduce side effects, but also maintain the drug at optimal therapeutic concentration over an extended period of time, thus increasing a therapeutic effect.

A typical example of such oral sustained-release formulations includes diffusion-type controlled-release formulations, particularly controlled-release capsule formulations having an insoluble coating. In such capsule formulations, the outer surface of a core (tablet or granule) containing a drug is coated with an insoluble coating. As the drug within the capsule is dissolved by digestive fluid infiltrated from the outside, the dissolved drug is diffused and released through the fine pores of the insoluble coating. These capsule formulations are commercially widely used because their preparation is relatively easy.

U.S. Pat. No. 4,772,475 (corresponding to Korean patent publication No. 93-7245; Yamanouchi Pharmaceutical Co., Ltd.) discloses a method for preparing an oral controlled-release pharmaceutical formulation containing tamsulosin HCl as an active ingredient. In order that tamsulosin HCl shows a sustained effect when administered orally, the disclosed method comprises: mixing tamsulosin HCl with a units-forming substance (i.e., crystalline cellulose as an excipient) that is not easily disintegrated in the gastrointestinal tract; adding a release-controlling agent/water mixture to the tamsulosin HCl/crystalline cellulose mixture, the release-controlling agent being selected from the group consisting of acrylic add polymers, acrylic add copolymers and mixtures thereof with cellulose derivatives; granulating the resulting mixture; and forming the granules into individual units (microcapsules or microspheres).

As an oral controlled-release tamsulosin HCl formulation, Harnal® capsule (sold from Yamanouchi Pharmaceutical Co., Ltd.) is prepared by the above prior method comprising: mixing tamsulosin HCl with crystalline cellulose; adding an aqueous emulsion of methacrylic acid copolymer to the mixture; granulating and drying the resulting mixture; spraying and coating and the granules with an aqueous solution of methacrylic acid copolymer; drying and sieving the coated granules. This prior method is being actually applied for the preparation of tamsulosin HCl sustained-release for- mulations. Here, the crystalline cellulose acts as not only an excipient to give a given bulkness, but also a release-controlling agent which helps the sustained release of tamsulosin HCl while maintaining the structure and strength of granules with methacrylic add copolymer, by virtue of its poor water solubility. However, in this prior method, if other general excipients (e.g., lactose and starch) than the crystalline cellulose are used together in the preparation of granules other than a final formulation, the release of tamsulosin HCl will be increased rapidly with the general excipients due to an accelerated increase in water infiltration with time, resulting in a rapid decrease in the physical strength of the granules. This makes the sustained release of tamsulosin HCl difficult.

In addition, in this prior method, since the mixing between a very small amount of tamsulosin HCl and a relatively large amount of crystalline cellulose is first performed, it is difficult to mix them uniformly. Also, to increase the integrity of a formulation, expensive special machines, such as an ultrahigh speed mixer and a fluidized bed granulator for centrifugation, needs to be used. Also, to control the release of a drug uniformly and consistently, only granules having a given size should be screened for the preparation of microcapsules or microspheres, and to provide the granules in the form of tablets or capsules, the addition of additional components is required. Thus, this prior art requires a complicated preparation process and necessarily involves an increase in production cost and a reduction in production yield. Furthermore, if the unit dose of an active ingredient, such as tamsulosin HCl, is low (0.1-0.2 mg/tablet or capsule), drug maldistribution during the mixing of the active ingredient and the excipient (referred to as 'units-forming substance') will occur to increase the possibility of occurrence of poor drug content uniformity, thereby increasing the possibility of a failure in maintaining uniform blood drug concentration in vivo.

Meanwhile, as another prior technique that is widely used for the preparation of a pharmaceutical formulation, a method using a solid dispersion may be mentioned. The solid dispersion is generally used according to a melting or solvent process.

In the melting process, a mixture of a poorly soluble drug and a carrier is dissolved by heat and then cooled. However, this process is limited in its applications, since it has problems in that the drug can be modified due to heating, and the properties (e.g., solubility) of the drug can vary depending on cooling rate.

Meanwhile, in the solvent method, a poorly soluble drug and a carrier are dissolved in a solvent capable of solubilizing both the two components, and then dried to remove the solvent. However, if cellulose or other polymers, or copolymers thereof, are used as the carrier, uniform stirring will be difficult due to the high viscosity of the carrier. Also, if the organic solvent is not sufficiently removed, the remaining solvent will affect the physical and chemical stabilities of the solid dispersion. Due to such problems, the solvent method has been considered to be unsuitable for use in industrial mass production.

Accordingly, it has been believed that it is highly difficult to formulate tamsulosin HCl into a tablet showing the satisfactory sustained-release of the drug. For this reason, a tamsulosin HCl sustained tablet has not yet been proposed.

DISCLOSURE OF THE INVENTION

The present inventors have performed extensive studies to develop a method for preparing an oral sustained-release tablet containing tamsulosin HCl, which can effectively solve various problems, including a sharp increase in production cost caused by the use of expensive special equipments and complicated preparation processes, low production yield, a possibility for drug content non-uniformity caused by the maldistribution of the active ingredient, and a possibility for residual organic solvent, which occur in the prior art of preparing an oral sustained-release capsule containing tamsulosin HCl as an active ingredient. As a result, the present inventors have found that the effective and easy preparation of a tamsulosin HCl sustained-release tablet can be achieved by use of an improved solid dispersion method (solvent method) that utilizes general equipment under general preparation conditions without using a complicated process or special equipment. On the basis of this discovery, the present inventors have conducted many studies, thereby completing the present invention.

A first object of the present invention is to provide a preparation method, which can prepare a tamsulosin HCl sustained-release tablet in a simple and efficient manner without using a complicated process or expensive special equipments, in which a low unit dose of tamsulosin HCl as an active pharmacological ingredient can be released at a controlled amount in a sustained-release manner in the gastrointestinal tract by controlling its release rate according to different pH environments in the gastrointestinal tract, so as to improve its bioavailability and minimize its side effects.

A second object of the present invention is to provide an economic method for preparing a tamsulosin HCl sustained-release tablet, which allows a reduction in production cost and a sharp increase in production yield.

A third object of the present invention is to provide a method for preparing a tamsulosin HCl sustained-release tablet, which can effectively eliminate the possibility of drug content non-uniformity resulting from the maldistribution of a low unit dose of tamsulosin HCl in the tablet.

A fourth object of the present invention is to provide a tamsulosin HCl sustained-release tablet prepared by the first to third objects of the present invention.

To achieve the above objects, the present invention provides a method for preparing a tamsulosin HCl sustained-release tablet by performing a mixing step after a dissolving step, which comprises the steps of: dissolving tamsulosin HCl in an organic solvent, dissolving a first hydroxypropylmethylcellulose phthalate (A) in the tamsulosin HCl solution to prepare a binder solution, and kneading the binder solution with an excipient mixture comprising a second hydroxypropylmethylcellulose phthalate (B) and glyceryl dibehenate.

According to the inventive preparing method, tamsulosin HCl as an active ingredient is dissolved in the binder solution. This can effectively eliminate the possibility of drug content non-uniformity in the tablet resulting from drug maldistribution, which can occur during the mixing of a very small amount of the active ingredient and a relatively large amount of the excipient.

Hydroxypropylmethylcellulose phthalate, which is used in the inventive preparation method, shows a change in solubility with pH, and thus, acts to control the dissolution pattern of tamsulosin HCl according to the change of gastrointestinal fluid. The content of hydroxypropylmethylcellulose phthalate in the binder solution is 10-150 parts by weight, preferably 25-120 parts by weight, and more preferably, 35-100 parts by weight, relative to one part of tamsulosin HCl. According to the inventive preparation method, a small amount of tamsulosin HCl which is sufficiently water-soluble is dispersed in hydroxypropylmethylcellulose phthalate, and thus, it is possible to prepare a solid dispersion which shows different dissolution patterns between gastric juices and intestinal juices by controlling dissolution rate according to pH.

The organic solvent, which can be used in the present invention, is not specifically limited if it can dissolve both tamsulosin HCl and hydroxypropylmethylcellulose phthalate. Preferred examples of the organic solvent include ethanol, ethylene chloride, a mixture thereof, and a mixture of any one of such solvents with water. The organic solvent is used at a suitable amount for use in the binder solution, for example, 100-500 parts by weight and preferably 180-300 parts by weight, relative to one part of tamsulosin HCl.

Moreover, hydroxypropylmethylcellulose phthalate is also used in a kneading and granulating step, its use amount in the kneading and granulating step is 50-500 parts by weight, preferably 100-350 parts by weight, and more preferably 200-350 parts by weight, relative to one part of tamsulosin HCl.

Optionally, hydroxypropylmethylcellulose phthalate may also be used in an additional excipient-adding step, in which case its use amount is 5-80 parts by weight, preferably 5-50 parts by weight, and more preferably 15-35 parts by weight.

Hydroxypropylmethylcellulose phthalate as described above is not substantially dissolved in gastric juice, but it is mainly dissolved in intestinal juices. For this reason, it contributes to the slow release of tamsulosin HCl by interaction with other excipients, such as glyceryl dibehenate or hydroxypropylmethylcellulose, while it shows different dissolution patterns between gastric juice and intestinal juice by the control of dissolution rate according to pH, thus contributing to the control or adjustment of release of tamsulosin HCl.

Glyceryl dibehenate and hydroxypropylmethylcellulose, which can be used in the present invention, are added for the preparation of a sustained-release tablet. Glyceryl dibehenate is hydrophobic in nature, so that it forms the interface between tamsulosin HCl and juice regardless of the kind of juice, to make the dissolution rate of the active ingredient slow. Glyceryl dibehenate is commercially available under the trademark of, for example, Compretol 888 ATO®. It is used at the amount of 10-200 parts by weight, preferably 25-150 parts by weight, and more preferably 50-100 parts by weight. Moreover, hydroxypropylmethylcellulose has the property of cellulose polymers. Namely, it shows intrinsic viscosity in an aqueous solution and is wetted and swollen in an aqueous solution. Due to such a property, it acts to prevent the rapid disintegration of a solid dispersion tablet to maintain the tablet form in gastrointestinal fluid and dissolution fluid for a sufficient time, thereby maintaining the surface ares of the tablet at a constant level. Accordingly, hydroxypropylmethylcellulose acts to ensure the sustained dissolution pattern of the tablets for an extended period of time and to reduce the deviation between the tablets. It is commercially available under the trademark of, for example, Metolose 60SH4000®. It is used at the amount of 10-300 parts by weight, and preferably 25-200. parts by weight, relative to one part of tamsulosin HCl.

In the inventive preparation method, additives that are conventionally used in the preparation of a sustained-release tablet may be used. Examples of the additives include excipients such as lactose, corn starch, cellulose polymer (e. g., hydroxypropylmethylcellulose, such as Metolose® 60SH-4000 or Metolose® 60SH-50, sold from ShinEtsu Co., Japan; hydroxypropylcellulose, a modified cellulose as a hydrophilic polymer, such as HPC-L® sold from ShinEtsu Co., Japan; and hydroxypropylcellulose phthalate, such as HPMCP® sold from ShinEtsu Co., Japan), mannitol, laolin, starch, powdered white sugar, and caldum phosphate, and lubricants, such as magnesium stearate, talc, caldum stearate, and fumed silicon dioxide. Preferred examples of the excipients include but are not limited to lactose, corn starch and cellulose polymer, and the preferred example of the lubricant includes but is not limited to magnesium stearate.

The inventive method for preparing the tamsulosin HCl sustained-release tablet comprises the following steps:

(A) Step of Providing Binder Solution

One part of tamsulosin hydrochloride as an active pharmacological ingredient is dissolved in 150-500 parts by weight and preferably 180-300 parts by weight of ethanol, methylene chloride, water or a mixture thereof. Then, a first hydroxypropylmethylcellulose phthalate (A) is dissolved in the tamsulosin HCl solution at the amount of 10-150 parts by weight, 25-120 parts by weight, and more preferably 35-100 parts by weight, to prepare a binder solution.

(B) Kneading and Granulating Step

The binder solution from the step (A) is kneaded with an excipient mixture comprising 50-500 parts by weight, preferably 100-350 parts by weight, and more preferably 200-350 parts by weight, of a second hydroxypropylmethylcellulose phthalate (B), and 10-200 parts by weight, 25-150 parts by weight, and 50-100 parts by weight, of glyceryl dibehenate. The kneaded material is then granulated. The excipient mixture may also comprise 300-700 parts by weight and preferably 400-550 parts by weight of lactose.

(C) Sieving Step

The granulated mixture is dried and then sieved.

(D) Additional Excipient-adding Step

Then, as an excipient, a third hydroxypropylmethylcellulose phthalate (C), hydroxypropylmethylcellulose, hydroxypropylcellulose and/or cornstarch are added to the sieved granules. In this step, a lubricant, such as magnesium stearate, is added.

The third hydroxypropylmethylcellulose phthalate (C), if used, is added at the amount of 5-80 parts by weight, preferably 5-50 parts by weight, and more preferably 15-35 parts by weight. Hydroxypropylmethylcellulose, if used, is added at the amount of 10-300 parts by weight, preferably 25-200 parts by weight. Hydroxypropylcellulose, if used, is added at the amount of 5-120 parts by weight, and preferably 15-100 parts by weight, and corn starch, if used, is added at the amount of 10-300 parts by weight, and preferably 50-150 parts.

Furthermore, the amount of addition of the lubricant is optional, but generally 3-40 parts by weight and preferably 5-20 parts by weight.

(E) Tableting Step

The granules are compressed into a tablet.

Accordingly, in the tablet according to the present invention, the sustained and controlled release of tamsulosin HCl is performed by hydroxypropylmethylcellulose phthalate, glyceryl dibehenate and a solid dispersion system thereof. Thus, if the amount of addition of such substances can be controlled so as to meet the objects of the present invention, they can be used in combination with various general excipients, including lactose and starches.

The inventive method for preparing the tamsulosin HCl sustained-release tablet can be conducted using conventional tablet preparation equipments and a simple process, and has high yield, resulting in high economic factor in an industrial viewpoint. Also, it nukes the distribution of tamsulosin HCl uniform and allows the control of release of tamsulosin HCl according to a change in pH (such that a change in dissolution pattern with pH, where tamsulosin HCl is dissolved in gastric juice to some extent and then mainly dissolved in intestinal juice, occurs, with the release rate of tamsulosin HCl being constant). For this reason, tamsluosin HCl in the tablet prepared according to the present invention can be released at uniformly controlled amounts in a sustained release manner within the stomach and the small intestines.

The dose of tamsulosin HCl as an active ingredient contained in the tamsulosin HCl sustained-release tablet can be suitably chosen according to various parameters, such as the age, sex, general health, disease to be treated and disease severity of a patient, and the in vivo absorption rate, inactivation rate and excretion rate of tamsulosin HCl. However, since the inventive tablet is excellent in sustained release properties and stability, the tamsulosin HCl in the inventive tablet is preferably administered at a dose of 0.1 mg/day (a tablet a day) or 0.2 mg/day (a tablet a day).

BRIEF DESCRIPTION OF DRAWINGS

FIG. 1 is a graphic diagram showing the average dissolution rate of tamsulosin HCl with time for the tamsulosin HCl tablet prepared in Example of the present invention, in which the dissolution rate was measured in a dissolution test under simulated human gastrointestinal conditions.

FIG. 2 is a graphic diagram showing the comparison of a change in blood tamsulosin HCl concentration with time between Beagle dogs that had been administered orally with the tamsulosin HCl tablet prepared in Example 4, and Beagle dogs that had been administered orally with the control tablet prepared in Comparative Example 1.

FIG. 3 is a graphic diagram showing the average dissolution rate of tamsulosin HCl with time for the tamsulosin HCl tablet prepared in Example 4 of the present invention and for the prior tamsulosin HCl sustained-release capsule (Harnal® capsule; sold from Yamanouchi Pharmaceutical Co., Ltd.) using coated granules as a control, in which the dissolution rate was measured in a dissolution test under simulated human gastrointestinal conditions.

FIG. 4 is a graphic diagram showing the comparison of a change in blood tamsulosin HCl concentration with time between volunteers who had been administered orally with the tamsulosin HCl tablet prepared in Example 4, and volunteers who had been administered orally with the prior tamsulosin HCl sustained-release capsule (Harnal capsule; sold from Yamanouchi Pharmaceutical Co., Ltd.) using coated granules as a control, in which the inventive tablet and the prior capsule were administered in a crossover trial.

BEST MODE FOR CARRYING OUT THE INVENTION

Hereinafter, the present invention will be described in detail by examples. It will however be obvious to a person skilled in the art that the present invention is not limited to or by the examples.

EXAMPLE 1

A sustained-release tablet having the following composition was prepared in the following manner:
Tamsulosin HCl 0.2 g
Hydroxypropylmethylcellulose phthalate (A) 10 g
Hydroxypropylmethylcellulose phthalate (B) 65 g
Lactose 99.8 g
Glyceryl dibehenate 15 g
Metolose 60SH-4000 (A) 15 g
Metolose 60SH-4000 (B) 20 g
Magnesium stearate 2 g Tamsulosin HCl was completely dissolved in 60 ml of a mixed organic solvent (ethanol:water=8:2) in which hydroxypropylmethylcellulose phthalate (A) was then dissolved to prepare a binder solution. Meanwhile, lactose, hydroxypropylmethylcellulose phthalate (B), Metolose 60SH-4000 (A) and glyceryl dibehenate were mixed with each other, to which the binder solution was then added and kneaded. The kneaded material was granulated and dried. The dried granules were sieved, and mixed with Metolose 60SH-4000 (B) as an excipient and magnesium stearate as a lubricant, and then compressed into tablets using a tableting machine. Each tablet contains 0.2 mg of tamsulosin HCl.

EXAMPLE 2

A sustained-release tablet having the following composition was prepared in the following manner:
Tamsulosin HCl 0.2 g
Hydroxypropylmethylcellulose phthalate (A) 10 g
Hydroxypropylmethylcellulose phthalate (B) 60 g
Lactose 94.8 g
Glyceryl dibehenate 15 g
Corn starch 20 g
Magnesium stearate 2 g Tamsulosin HCl was completely dissolved in 50 ml of a mixed organic solvent (ethanol:water=8:2) in which hydroxypropylmethylcellulose phthalate (A) was then dissolved to prepare a binder solution. Meanwhile, lactose, hydroxypropylmethylcellulose phthalate (B) and glyceryl dibehenate were mixed with each other, to which the binder solution was then added and kneaded. The kneaded material was granulated and dried. The dried granules were sieved, and additionally mixed with corn starch as an excipient and magnesium stearate as a lubricant, and then compressed into tablets using a tableting machine. Each tablet contains 0.2 mg of tamsulosin HCl.

EXAMPLE 3

A sustained-release tablet having the following composition was prepared in the same manner as in Example 1 except that low-substituted hydroxypropylcellulose 11 was added:
Tamsulosin HCl 0.2 g
Hydroxypropylmethylcellulose phthalate (A) 20 g
Hydroxypropylmethylcellulose phthalate (B) 70 g
Lactose 104.8 g
Glyceryl dibehenate 15 g
low-substituted hydroxypropylcellulose 11 15 g
Metolose 60SH-4000 (B) 30 g
Magnesium stearate 2 g

EXAMPLE 4

A sustained-release tablet having the following composition was prepared in the same manner as in Example 2 except that the mixed organic solvent was used at the amount of 40 ml, and hydroxypropylmethylcellulose phthalate was added to the dried granules in the additional excipient-adding step:
Tamsulosin HCl 0.2 g
Hydroxypropylmethylcellulose phthalate (A) 10 g
Hydroxypropylmethylcellulose phthalate (B) 55 g
Hydroxypropylmethylcellulose phthalate (C) 5 g
Lactose 89.8 g
Glyceryl dibehenate 15 g
Corn starch 20 g
Magnesium stearate 2 g

EXAMPLE 5

A sustained-release tablet having the following composition was prepared in the same manner as in Example 4 except that hydroxypropylcellulose (Metolose 60SH4000) was added to the dried granules in the additional excipient-adding step:
Tamsulosin HCl 0.2 g
Hydroxypropylmethylcellulose phthalate (A) 10 g
Hydroxypropylmethylcellulose phthalate (B) 55 g
Metolose 60SH4000 5 g Lactose 89.8 g
Glyceryl dibehenate 15 g
Corn starch 20 g
Magnesium stearate 2 g

EXAMPLE 6

A sustained-release tablet was prepared in the same manner as in Example 2 except that corn starch was used at the amount of 28 g.

EXAMPLES 7-10

A sustained-release tablet was prepared in the same manner as in Example 1 except that hydroxypropylmethylcellulose phthalate (B) was used at the amounts of 20 g, 30 g, 40 g and 50 g.

EXAMPLES 11-13

A sustained-release tablet was prepared in the same manner as in Example 3 except that hydroxypropylmethylcellulose phthalate (A) was used at the amounts of 5 g, 10 g and 15 g.

EXAMPLES 14-16

A sustained-release tablet was prepared in the same manner as in Example 4 except that glyceryl dibehenate was used at the amounts of 5 g, 10 g and 30 g.

EXAMPLE 17

A sustained-release tablet was prepared in the same manner as in Example 4 except that 40 ml of a mixture of methanol and methylene chloride (5:5) was used as the mixed organic solvent.

COMPARATIVE EXAMPLE 1

A conventional tablet having the following composition was prepared:
Tamsulosin HCl 0.2 g
Lactose 150 g
Sodium starch glyconate 5 g
Polyvinylpyrrolidone 10 g
Magnesium stearate 2 g

TEST EXAMPLE 1

The tablets prepared in Examples 2, 4, 5, 11, 14 and 16 were subjected to a dissolution test under simulated gastrointestinal conditions in the following manner.

1) Preparation of Test Solution

Preparation of test solution The test was conducted according to the dissolution test method 2 described in Korea Pharmacopeia. For the preparation of a test solution, 1 ml of a polysorbate 80 solution (3→200) was added to 500 ml of a first solution described in a disintegration test method. At 2 hours after the initiation of dissolution test, the test solution was replaced with 500 ml of phosphate buffer solution (37±0.5° C.; pH 7.2).

2) Operation

The test was performed using high-performance liquid chromatography (HPLC) under the following conditions:

Detector: UV absorption spectrophotometer (measurement wavelength: 225 nm)

Column: Capelle Pak® 3 mm ×150 mm, 5 µm $C_{18}$ (ODS).

Column temperature: 40° C.

Mobile phase: a mixture of 0.05N perchloric acid and acetonitrile (7:3)

Injection: 50 µl (Test Results)

The test results are shown in FIG. 1. In FIG. 1, the symbol -□- represents the average dissolution rate of tamsulosin HCl in the tablet prepared in Example 2, and the symbol -◇- in the tablet prepared in Example 4, the symbol -▯- in the tablet prepared in Example 5, and the symbol -+- in the tablet prepared in Example 11, and the symbol -X- in the tablet prepared in Example 14, and the symbol -O- in the tablet prepared in Example 16.

TEST EXAMPLE 2

The tablet prepared in Example 4 was used as the test sample of the invention, and the conventional tablet prepared in Comparative Example 1 was used as a control. Each of the tablets was administered orally to three beagle dogs in a crossover trial. Then, changes in blood tamsulosin HCl concentration with time were measured for comparison.

(Test Results)

The test results are shown in Table 1 below and FIG. 2. In FIG. 2, the symbols -O- and -●- represent the average blood concentrations of tamsulosin HCl with time in the tablets prepared in Comparative Example 1 and Examples 4, respectively.

As evident from the test results, the tablet prepared in Example 4 showed the obvious pattern of a sustained-release tablet which shows a long-term action.

TABLE 1

| | | Blood concentration of tamslusion HCl with time (ng/ml) | | | | | | | | | | | |
|---|---|---|---|---|---|---|---|---|---|---|---|---|---|
| | | 0. | 0.5 | 1.0 | 2.0 | 3.0 | 4.0 | 5.0 | 6.0 | 8.0 | 10.0 | 12.0 | 24.0 |
| Comparative Example 1 | A | 0.0 | 18.4 | 23.0 | 13.0 | 7.1 | 4.6 | 5.7 | 4.0 | 3.5 | 0.9 | 1.2 | 0.0 |
| | B | 0.0 | 11.7 | 27.8 | 13.7 | 10.2 | 8.6 | 7.3 | 4.4 | 3.8 | 2.7 | 0.0 | 0.4 |
| | C | 0.0 | 15.2 | 24.5 | 21.8 | 12.8 | 9.3 | 6.9 | 6.9 | 5.3 | 1.8 | 0.0 | 0.0 |
| Example 4 | A | 0.0 | 2.7 | 6.1 | 10.6 | 8.3 | 9.6 | 8.6 | 6.7 | 5.2 | 3.9 | 3.1 | 1.1 |
| | B | 0.0 | 7.5 | 8.3 | 13.3 | 13.3 | 14.5 | 12.6 | 14.8 | 11.3 | 8.6 | 5.5 | 0.0 |
| | C | 0.0 | 1.7 | 7.4 | 10.5 | 12.2 | 10.8 | 10.5 | 8.7 | 6.7 | 5.5 | 3.8 | 0.0 |
| Comparative Example 1 | Average | 0.0 | 15.1 | 25.1 | 16.2 | 10.0 | 7.5 | 6.6 | 5.1 | 4.2 | 1.8 | 0.4 | 0.1 |
| Example 4 | Average | 0.0 | 3.9 | 7.2 | 11.5 | 11.2 | 11.6 | 10.6 | 10.0 | 7.7 | 6.0 | 4.1 | 0.4 |

TEST EXAMPLE 3

The sustained-release tablet containing 0.2 mg of tamsulosin HCl prepared in Example 4 was used as the test sample of the invention, and a prior tamsulosin HCl capsule (Harnal® capsule, sold from Yamanouchi Pharmaceutical Co., Ltd.) was used as a control. The tablet and the capsule were subjected to a dissolution test under simulated human gastrointestinal conditions in the same manner as in Test Example 1 above.

(Test Result)

The results of the dissolution test under simulated human gastrointestinal conditions are shown in FIG. 3. In FIG. 3, the symbols-O-and-●-represent the test results for the tablet prepared in Example 4, and the prior capsule (Harnal® capsule), respectively. As evident from the test results, the tamsulosin HCl tablet according to the present invention showed substantially the same dissolution pattern as that of the prior tamsulosin HCl capsule.

TEST EXAMPLE 4

The tablet containing 0.2 mg of tamsulosin HCl prepared in Example 4 was used as the test sample of the invention, and the prior tamsulosin. HCl capsule (Harnal® capsule, sold from Yamanouchi Pharmaceutical Co., Ltd.) containing 0.2 mg of tamsulosin HCl was used as a control. Each of the tablet and the capsule was administered orally to 32 healthy adult male volunteers in 2×2 crossover trial. Then, the drug concentration in blood with time for each volunteer was measured.

(Test Results)

The average blood drug concentrations with time, which had been measured after administering the inventive sample and the control to 32 volunteers, are shown in FIG. 4. In FIG. 4, the symbols-O-and-●-represent the average blood concentration of tamsulation HCl with time for the tablet prepared in Example 4, and the prior capsule (Harnal® capsule), respectively.

TEST EXAMPLE 5

The sustained-release tablets each containing 0.2 mg of tamsulosin HCl, which had been prepared in Example 4, were stored under conditions of room temperature and 40° C. and 75% RH for six months. Then, the tablets were subjected to a dissolution test under simulated human gastrointestinal conditions in the same manner as in Test Example 1, and their stability with time was evaluated.

(Test Results)

The evaluation results are given in Table 2 below. As evident from Table 2, the tablets showed a very low change in solubility with time, indicating that they have excellent stability with time.

TABLE 2

|  |  | 0 | 2 hr | 3 hr | 5 hr |
|---|---|---|---|---|---|
| Within one day after preparation | A | 0.0 | 24.6% | 57.2% | 89.6% |
|  | B | 0.0 | 23.5% | 56.1% | 89.9% |
|  | C | 0.0 | 27.1% | 58.8% | 84.5% |
|  | Average | 0.0 | 25.0% | 57.4% | 88.0% |
| Six months after preparation (stored at RT and atmospheric conditions) | A | 0.0 | 26.0% | 58.8% | 90.9% |
|  | B | 0.0 | 24.8% | 55.1% | 88.5% |
|  | C | 0.0 | 26.3% | 59.6% | 89.4% |
|  | Average | 0.0 | 25.7% | 57.8% | 89.6% |
| Six months after preparation (stored at 40° C. and 75% RH conditions) | A | 0.0 | 23.3% | 56.8% | 89.4% |
|  | B | 0.0 | 26.8% | 55.6% | 92.5% |
|  | C | 0.0 | 25.5% | 58.3% | 90.2% |
|  | Average | 0.0 | 25.2% | 56.9% | 90.7% |

TEST EXAMPLE 6

Using the tablets prepared in Example 4, three samples were prepared in different batches in the same manner as in Test Example 1 above. Then, the batches were subjected to a dissolution test in simulated human gastrointestinal conditions, and the deviation between the batches was evaluated.

(Test Results)

The evaluation results are given in Table 3 below. As evident from Table 3, the amount of deviation between the batches was very low, being within an acceptable range.

TABLE 3

|  | 0 | 2 hr | 3 hr | 5 hr |
|---|---|---|---|---|
| A | 0.0 | 25.6% | 55.7% | 90.1% |
| B | 0.0 | 24.8% | 55.1% | 90.4% |
| C | 0.0 | 26.2% | 56.3% | 89.7% |

EXAMPLE 7

A residual solvent test was performed on the tablets prepared in Examples 4 and 17.

(Test Results)

The test results are given in Table 4 below, and showed that an organic solvent was effectively removed.

TABLE 4

|  | Solvent | ICH standard* | Measured value |
|---|---|---|---|
| Example 4 | Ethanol | Less than 5,000 ppm | 288 ppm |
| Example 17 | Ethanol | Less than 5,000 ppm | 96 ppm |
|  | Methylene chloride | Less than 600 ppm | 29 ppm |

*ICH: International conference on harmonization of technical requirements for registration of pharmaceuticals for human use.

INDUSTRIAL APPLICABILITY

As described above, in the inventive method for preparing the tamsulosin HCl sustained-release tablet, the mixture obtained by first dissolving tamsulosin HCl dissolved in the mixed organic solvent and then dissolving hydroxypropylmethylcellulose phthalate in the tamsulosin HCl solution is used as a binder without a separate drying process. This can effectively eliminate various problems, such as residual organic solvent, and stirring difficulty caused by high viscosity at the end of drying, which occur in the case of the preparation of a solid dispersion using an active ingredient and a carrier. Also, according to the present invention, since the tamsulosin HCl-containing binder solution is kneaded with excipients uniformly, the content uniformity of the active ingredient can be easily achieved and the organic solvent can be easily removed as a result of the improvement of drying efficiency, to eliminate problems caused by residual organic solvent. Furthermore, according to the present invention, the solid dispersion where the active ingredient is distributed uniformly can be effectively prepared by conventional steps, such as mixing, kneading, sieving, additional mixing and tableting, without a need for the use of expensive equipments and additional complex processes. This can achieve the simplification of a preparation process, the sharp reduction of production cost, the increase of production yield, and the uniformity of drug content. In addition, the tamsulosin HCl sustained-release tablet prepared according to the present invention allows tamsulosin HCl to be released at uniformly controlled amounts in a sustained-release manner in vivo by controlling drug release according to different pH environments in vivo, so that it shows improved bioavailability and minimized side effects.

The invention claimed is:

1. A method for preparing a tamsulosin HCl sustained-release tablet, which comprises the steps of:
    (A) dissolving tamsulosin HCl in a solvent and then dissolving a first hydroxypropylmethylcellulose phthalate in the tamsulosin HCl to prepare a binder solution;
    (B) kneading the binder solution with an excipient mixture comprising a second hydroxypropylmethylcellulose phthalate and glyceryl dibehenate, and granulating the kneaded material to provide granules; and
    (C) compressing the granules into a tablet;
    wherein in step (A), the amount of the first hydroxypropylmethylcellulose phthalate is 10 to 150 parts by weight relative to 1 part by weight of tamsulosin HCl, and in step (B), the amount of the second hydroxypropylmethylcellulose phthalate in the excipient mixture is 50 to 500 parts by weight relative to 1 part by weight of tamsulosin HCl and the amount of the glyceryl dibehenate in the excipient mixture is 10 to 200 parts by weight relative to 1 part by weight of tamsulosin HCl.

2. The method of claim 1, which further comprises the step (B1) of drying and then sieving the granules, after the kneading and granulating step (B).

3. The method of claim 2, wherein the solvent is at least one selected from the group consisting of ethanol, methylene chloride and water.

4. The method of claim 3, wherein the solvent is added at the amount of 180-300 parts by weight relative to one part by weight of tamsulosin HCl.

5. The method of claim 2, wherein the first hydroxypropylmethylcellulose phthalate in the binder solution-preparing step (A) is added at the amount of 25-120 parts by weight relative to one part by weight of tamsulosin HCl, and the second hydroxypropylmethylcellulose phthalate in the kneading and granulating step (B) is added at the amount of 100-350 parts by weight relative to one part by weight of tamsulosin HCl.

6. The method of claim 2, wherein the glyceryl dibehenate in the kneading and granulating step (B) is added at the amount of 25-150 parts by weight relative to one part by weight of tamsulosin HCl.

7. The method of claim 2, wherein lactose is added in the kneading and granulating step (B) at the amount of 300-700 parts by weight relative to one part by weight of tamsulosin HCl.

8. The method of claim 1, wherein the solvent is at least one selected from the group consisting of ethanol, methylene chloride and water.

9. The method of claim 8, wherein the solvent is added at the amount of 180-300 parts by weight relative to one part by weight of tamsulosin HCl.

10. The method of claim 1, wherein the first hydroxypropylmethylcellulose phthalate in the binder solution-preparing step (A) is added at the amount of 25-120 parts by weight relative to one part by weight of tamsulosin HCl, and the second hydroxypropylmethylcellulose phthalate in the kneading and granulating step (B) is added at the amount of 100-350 parts by weight relative to one part by weight of tamsulosin HCl.

11. The method of claim 1, wherein the glyceryl dibehenate in the kneading and granulating step (B) is added at the amount of 25-150 parts by weight relative to one part by weight of tamsulosin HCl.

12. The method of claim 1, wherein lactose is added in the kneading and granulating step (B) at the amount of 300-700 parts by weight relative to one part by weight of tamsulosin HCl.

13. The method of claim 2, which further comprises the additional excipient-adding step (B2) of adding at least one substance selected from the group consisting of a third hydroxypropylmethylcellulose phthalate, hydroxypropylmethylcellulose and corn starch, to the granules, after the kneading and granulating step (B) or the sieving step (B1).

14. The method of claim 13, wherein, at the excipient-adding step (B2), the third hydroxypropylmethylcellulose phthalate, if used, is added at the amount of 5-80 parts by weight relative to one part by weight of tamsulosin HCl, the hydroxypropylmethylcellulose, if used, is added at the amount of 10-300 parts by weight relative to one part by weight of tamsulosin HCl, and the corn starch, if used, is added at the amount of 10-300 parts by weight relative to one part by weight of tamsulosin HCl.

15. A tamsulosin HCl sustained-release tablet prepared by the method of claim 1.

16. A tamsulosin HCl sustained-release tablet prepared by the method of claim 2.

17. A tamsulosin HCl sustained-release tablet prepared by the method of claim 9.

18. A tamsulosin HCl sustained-release tablet prepared by the method of claim 14.

* * * * *